(12) United States Patent
Knowles et al.

(10) Patent No.: US 12,318,590 B2
(45) Date of Patent: Jun. 3, 2025

(54) INJECTOR PEN ASSEMBLY

(71) Applicant: Shaily Engineering Plastics Limited, Gujarat (IN)

(72) Inventors: Stephen Knowles, Datchet (GB); Simon Collings, Datchet (GB)

(73) Assignee: SHAILY ENGINEERING PLASTICS LTD., Gujarat (IN)

( * ) Notice: Subject to any disclaimer, the term of this patent is extended or adjusted under 35 U.S.C. 154(b) by 936 days.

(21) Appl. No.: 17/292,222

(22) PCT Filed: Jun. 22, 2020

(86) PCT No.: PCT/GB2020/051505
§ 371 (c)(1),
(2) Date: May 7, 2021

(87) PCT Pub. No.: WO2020/254834
PCT Pub. Date: Dec. 24, 2020

(65) Prior Publication Data
US 2021/0402099 A1 Dec. 30, 2021

(30) Foreign Application Priority Data
Jun. 21, 2019 (GB) .................................... 1908917

(51) Int. Cl.
*A61M 5/315* (2006.01)
*A61M 5/24* (2006.01)

(52) U.S. Cl.
CPC .......... *A61M 5/31551* (2013.01); *A61M 5/24* (2013.01); *A61M 5/31585* (2013.01); *A61M 2005/2492* (2013.01); *A61M 2207/00* (2013.01)

(58) Field of Classification Search
CPC ................ A61M 5/31551; A61M 5/24; A61M 5/31585; A61M 2005/2492;
(Continued)

(56) References Cited

U.S. PATENT DOCUMENTS 10,034,982 B2 7/2018 Plumptre
2014/0074042 A1* 3/2014 Schneider ......... A61M 5/31543
604/220

(Continued)

FOREIGN PATENT DOCUMENTS

JP 2005508205 A 3/2005
JP 2012532635 A 12/2012
(Continued)

OTHER PUBLICATIONS

Combined Search and Examination Report for Application No. GB1908917.6, Dec. 9, 2019, 5 pages.
(Continued)

*Primary Examiner* — Michael J Tsai
*Assistant Examiner* — Neeraja Gollamudi
(74) *Attorney, Agent, or Firm* — Kilyk & Bowersox, P.L.L.C.

(57) ABSTRACT

An injector pen is provided that includes a cartridge housing 2, a dose selector housing 10 and a nut 18 for coupling the two housings 2,10 together. The dose selector housing 10 defines an intermediate axial position, where the nut 18 can be temporarily retained in the dose selector housing 10 to form a sub-assembly suitable for transport to a different location. During final assembly of the injector pen, the cartridge housing 2 securely engages with the nut 18 and displaces the nut 18 from the intermediate axial position to a final axial position.

13 Claims, 5 Drawing Sheets

(58) Field of Classification Search
CPC ...... A61M 2207/00; A61M 2005/2407; A61M 5/31533; A61M 5/2422; A61M 2005/2485; A61M 5/315; A61M 5/31525; A61M 5/31545; A61M 5/31548; A61M 5/31563; A61M 5/31576; A61M 5/31583; A61M 5/31565
See application file for complete search history.

(56) References Cited

U.S. PATENT DOCUMENTS

| | | |
|---|---|---|
| 2015/0112277 A1 | 4/2015 | Groeschke et al. |
| 2017/0259011 A1* | 9/2017 | Nielsen ............... A61M 5/3158 |
| 2018/0272070 A1 | 9/2018 | Bengtsson |
| 2019/0167909 A1* | 6/2019 | Atterbury ......... A61M 5/31566 |

FOREIGN PATENT DOCUMENTS

| | | |
|---|---|---|
| WO | 02092153 A2 | 11/2002 |
| WO | 2011003979 A1 | 1/2011 |
| WO | 2019/072826 A1 | 4/2019 |

OTHER PUBLICATIONS

International Search Report and written opinion for Application No. PCT/GB2020/051505, with notification, mailed Sep. 30, 2020, 15 pages.

* cited by examiner

INJECTOR PEN ASSEMBLY

FIELD OF THE INVENTION

The invention relates to injector pens that contain a drug cartridge and comprise means for selecting and delivering one or more doses of a drug from the cartridge through a hypodermic needle. In particular, it relates to the method and coupling by which the dose selector housing and cartridge housing of such a pen may be assembled and secured together for ease of manufacture and transport.

BACKGROUND OF THE INVENTION

Injector pens are typically assembled from two main components. The first component is a cartridge housing that contains a drug cartridge, from which a desired dose of a drug may be expelled by driving forwards a piston located inside the cartridge. The cartridge housing also comprises an attachment for a hypodermic needle, through which the drug can be delivered from the cartridge to a subject. The cartridge may contain a single, measured dose of the drug but more commonly it contains a quantity sufficient to deliver multiple doses.

The second main component of the injector pen is a dose selector, contained in a dose selector housing, which is used in a first mode to select the desired dose of drug. In a second mode, the dose selector then delivers the drug to a patient by moving a piston rod through a distance that corresponds to the selected dose. The piston rod extends out of the dose selector housing and into the cartridge housing to engage the piston of the drug cartridge. Various mechanisms are known for selecting the dose, typically by withdrawing a dose delivery button along a linear or helical path, through an axial distance that measures the dose to be selected. The dose delivery button is then pushed forwards to return to its starting position, while a transmission mechanism converts the forward movement of the button into forward movement of the piston rod through a proportionate distance (sometimes with a simultaneous rotational movement of the piston rod). The details of the dose selection mechanism are not relevant to the present invention, which is applicable to all dose selectors of the general form described.

Some injector pens are designed so that when the supply of drug in the cartridge is exhausted a replacement cartridge can be fitted into the cartridge housing and the position of the piston rod can be reset to resume use of the pen. On the other hand, the present invention is most suitable for pens that are not reusable. The pen may be used to deliver single dose or multiple doses but when the cartridge is empty, or when less than a predetermined minimum dose remains, the pen is disposed of.

There are various reasons why it may be undesirable to insert the drug cartridge into the injector pen when the pen is initially manufactured. Such pens are typically manufactured by a medical equipment company then supplied to a drugs company for onward distribution, and it is more efficient for the drugs company to provide and fit the drug cartridge. Alternatively, the unfilled pens and the drug cartridges can be supplied separately, for final assembly by a third party such as a drug distributor or a health service. Separating initial manufacture from final assembly in this way allows a single model of pen to be used for multiple types of drug, which simplifies both the inventory and supply chain functions. Also, certain drugs have a limited shelf-life or have particular storage requirements such as a need for refrigeration, so it is beneficial to allow the unfilled pens to be distributed and stored without being subject to such limitations. Consistently with this distribution model, it is desirable that the pens following their initial manufacture should be in a condition suitable for safe transport and storage, leaving the steps of inserting the drug cartridge and final assembly of the pens to be as simple and reliable as possible.

SUMMARY OF THE INVENTION

The invention provides a sub-assembly for an injector pen as defined in claim 1.

The invention further provides:
- a method of forming an injector pen sub-assembly as defined in claim 9;
- a method of assembling an injector pen from a sub-assembly, as defined in claim 10.

It will be understood that the initial manufacture (claim 9) and the final assembly (claim 10) need not take place in the same location or the same legal jurisdiction.

In this specification, the term "distal" refers to the end of the pen at which the hypodermic needle is attached, while the term "proximal" refers to the end of the pen where the dose delivery button is located. "Forwards" refers to the direction towards the distal end of the pen. If two elements are "releasably engaged" or one is "releasably retained" in the other, then the elements are at least temporarily held together to prevent them being accidentally separated during normal use, transport or storage of the article of which they form part. However, they are designed to be separated easily when it is desired to do so, for example by applying a certain level of force or by manipulating the elements in a specific way. In contrast, if two elements are "securely engaged", then they are designed to be permanently attached to one another. The permanence of the attachment may be, among other reasons, because attempting to separate the elements would risk damaging them or because the connecting parts of the respective elements cannot be easily accessed in order to release the engagement between them.

Figure 1:
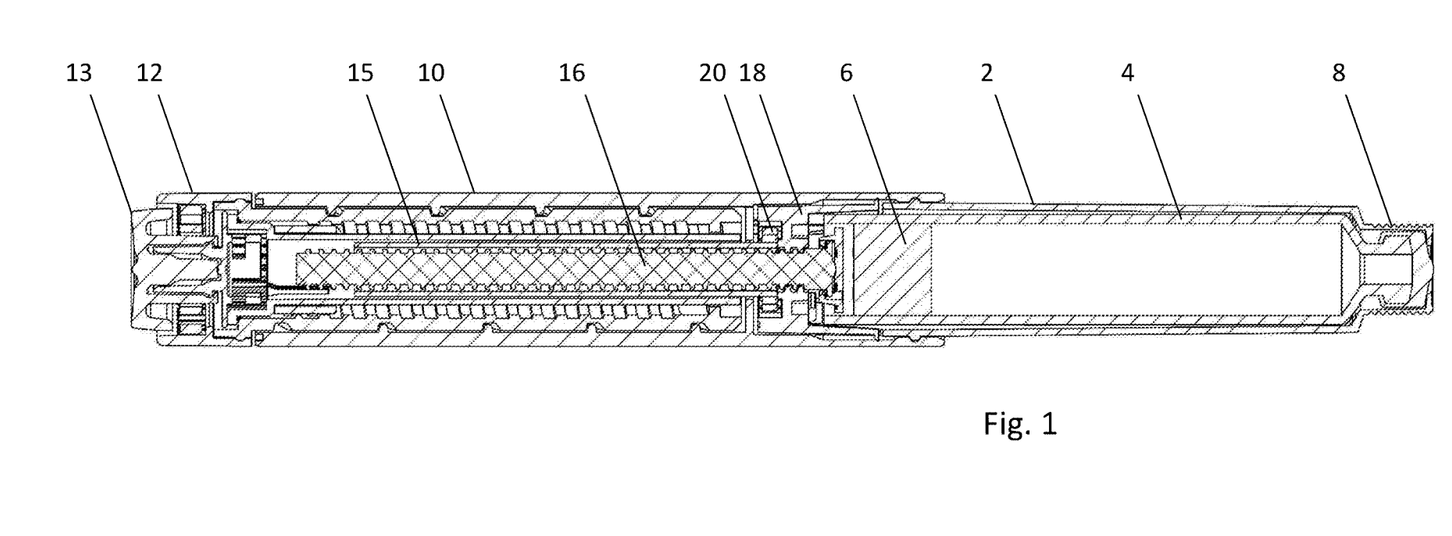
FIG. 1 is a longitudinal section of an assembled injector pen according to the invention.

FIG. 1 illustrates, in longitudinal section, an assembled injector pen according to the invention. At the distal end of the pen is a cartridge housing 2, which contains a drug cartridge 4. A piston 6 is located inside the cartridge 4 and can be urged forwards to displace a dose of a drug from the cartridge 4. The cartridge housing 2 comprises a thread 8 or other suitable means for attaching a hypodermic needle (not shown), through which the dose of drug can be delivered into the skin of a patient or other subject.

Figure 2:
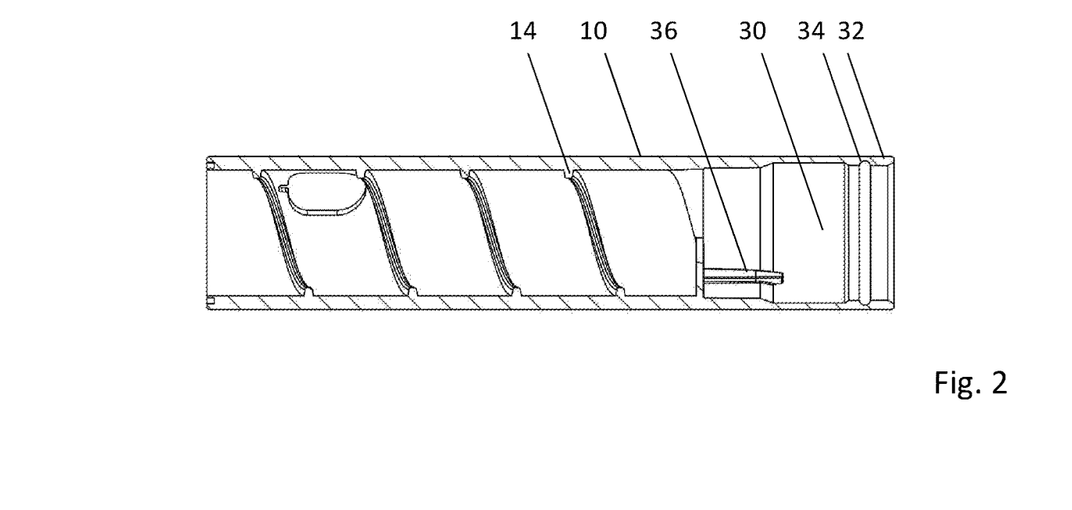
FIG. 2 is a longitudinal section of the dose selector housing of the injector pen of FIG. 1.

At the proximal end of the injector pen is a dose selector housing 10. The dose selector housing 10 contains a dose selector 12, which is used to set and then deliver doses of the drug from the pen. The dose selector 12 is withdrawn in the proximal direction through a distance that determines the dose to be set. As seen in FIG. 2, in the illustrated embodiment of the invention the dose selector housing 10 has an internal thread 14 to guide the movement of the dose selector 12 along a helical path. However, that is not essential: in other embodiments (not illustrated) the dose selector 12 moves along a straight, axial path. After the desired dose has been set, a dose delivery button 13 on the proximal end of the pen is pushed forwards to return the dose selector 12 to its starting position, while an internal gearing mechanism 15 converts the axial movement of the dose selector 12 into a proportionate—though not necessarily equal—degree of axial movement of a piston rod 16. The details of the transmission 15 differ between types of pen and are not relevant to the present invention so they will not be described further.

The piston rod 16 protrudes from the distal end of the dose selector housing 10 and extends into the cartridge housing 2. A distal end of the piston rod 16 engages the piston 6 so that forward movement of the piston rod 16 through the distance determined by the dose selector 12 displaces the desired dose of drug from the drug cartridge 4.

A nut 18 is located between the cartridge housing 2 and the dose selector housing 10 and serves to couple the two housings 2,10 together, as described below. The nut 18 also guides the piston rod 16 as it emerges from the dose selector housing 10. In the illustrated embodiment of the invention, the nut 18 has a threaded engagement with the piston rod 16 but that is not essential; in other embodiments (not illustrated) the piston rod 16 is in sliding engagement with the nut 18. If the cartridge 4 contains multiple doses, the dose selector 12 may be operated through multiple cycles of forward and backward movement but a ratchet mechanism 20 acting between the nut 18 and the transmission mechanism 15 ensures that the piston rod 16 can only move forwards.

Figure 3:
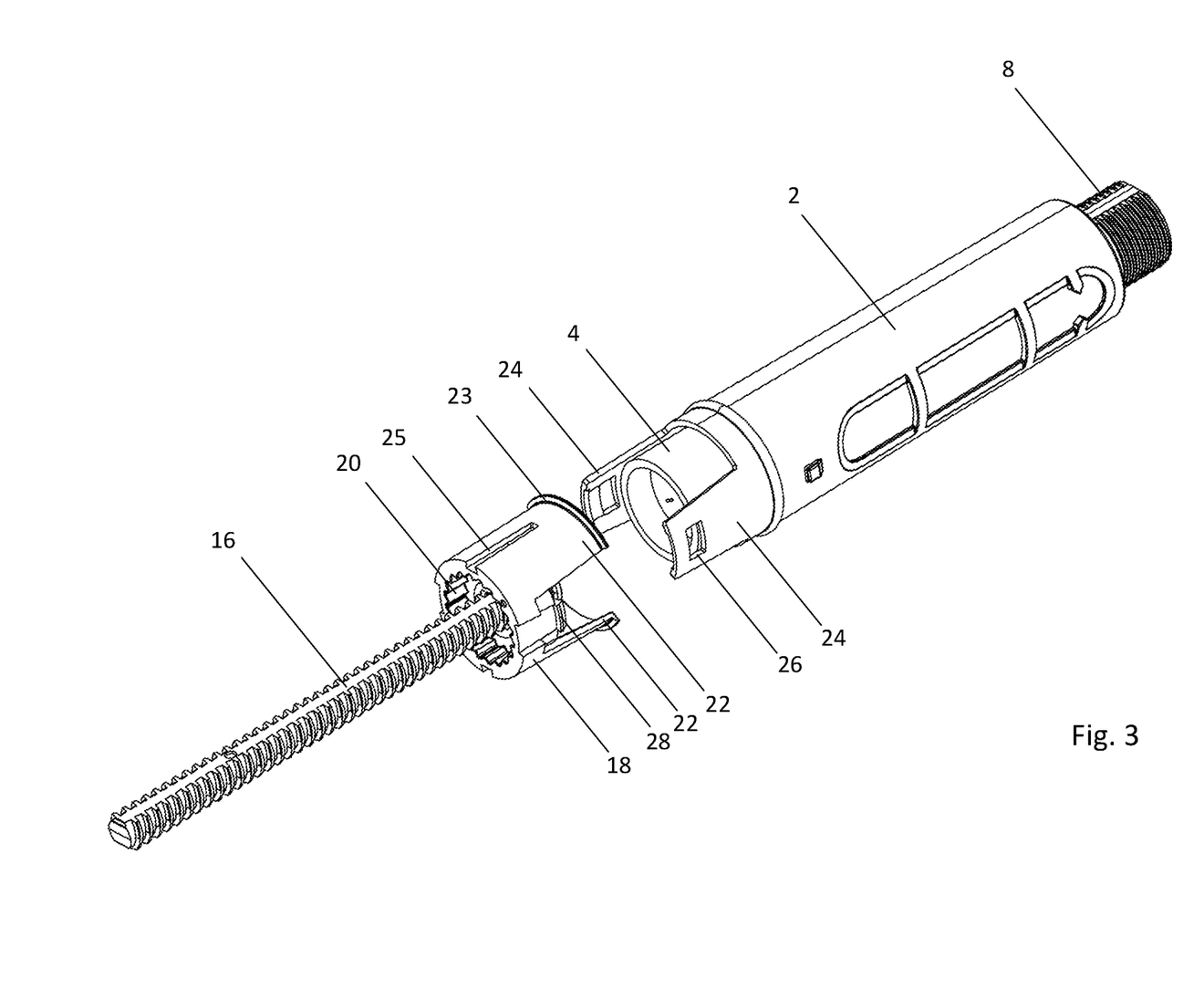
FIG. 3 is a perspective view of the cartridge housing, nut and piston rod of the injector pen of FIG. 1, prior to assembly.

In the perspective view of FIG. 3, the dose selector housing 10 has been omitted in order to show the relationship between the nut 18 and the cartridge housing 2 more clearly. It may be seen that the nut 18 generally cup-shaped, being open at its distal end to receive the proximal end of the drug cartridge 4. The distal end of the nut 18 terminates in two alignment arms 22 that extend in the distal direction towards the cartridge housing 2. Similarly, the proximal end of an outer wall of the cartridge housing 2 terminates in two alignment arms 24 that extend in the proximal direction towards the nut 18. The respective pairs of alignment arms 22,24 have complementary shapes so that they can interdigitate and fit together when the nut 18 and the cartridge housing 2 are brought into engagement. It will be understood that in other embodiments the number of alignment arms 22 on the nut 18 and the number of alignment arms 24 on the cartridge housing 2 could be greater than two, provided the respective numbers are equal. Each alignment arm 22 of the nut 18 carries a segment of an outwardly extending lip 23 at or near its distal end. The lip 23 thus extends discontinuously around the circumference of the nut 18. Two channels 25 are formed in an outer wall of the nut 18 and extend axially from the base of the nut 18 along part of the length of the respective alignment arms 22. In other embodiments (not illustrated) the number of axial channels 25 could be greater than two. There is typically, but not necessarily, one channel 25 formed in each alignment arm 22.

Each alignment arm 24 of the cartridge housing 2 comprises a recess 26. The recess could be blind but preferably, as illustrated, the recess 26 is formed as an aperture that pierces the alignment arm 24. In each gap between adjacent alignment arms 22 of the nut 18 a clip 28 is formed, which snaps into the corresponding recess 26 when the nut 18 and the cartridge housing 2 are brought together and prevents them being pulled apart again, thereby securely engaging the nut 18 with the cartridge housing 2. In alternative embodiments the nut 18 could comprise the recesses and the alignment arms 24 of the cartridge housing 2 could comprise the clips. Other alternative mechanisms for providing that the nut 18 and the cartridge housing 2 can be pushed axially together but not easily pulled apart again will be apparent to the reader.

As seen in FIG. 2, the dose selector housing 10 comprises a cavity 30 with an opening in its distal end for receiving the nut 18. The neck 32 of the cavity 30 has a thicker wall than the main body of the dose selector housing 10 to constrict the opening. An annular indent 34 is formed within the thickened wall of the neck 32. A pair of opposite, axially extending ribs 36 project inwards into the cavity 30. The axial ribs 36 of the dose selector housing 10 correspond in number and position to the axial channels 25 of the nut 18.

FIGS. 4A to 4D and 5A to 5B show the sequence of steps by which the dose selector housing 10, the nut 18 and the cartridge housing 2 are assembled to form an injector pen. Only the region around the nut 18 is shown in these figures; it should be understood that the dose selector housing 10 extends below the curved line at the bottom of each figure and that the cartridge housing 2 extends above the curved line at the top of FIGS. 4C, 4D, 5A and 5B. The dose selector housing 10 is cut away on a plane along the axis to show the relationship between the various components. For clarity, the piston rod 16 and the cartridge 4 are not shown in these figures.

Figure 4A:
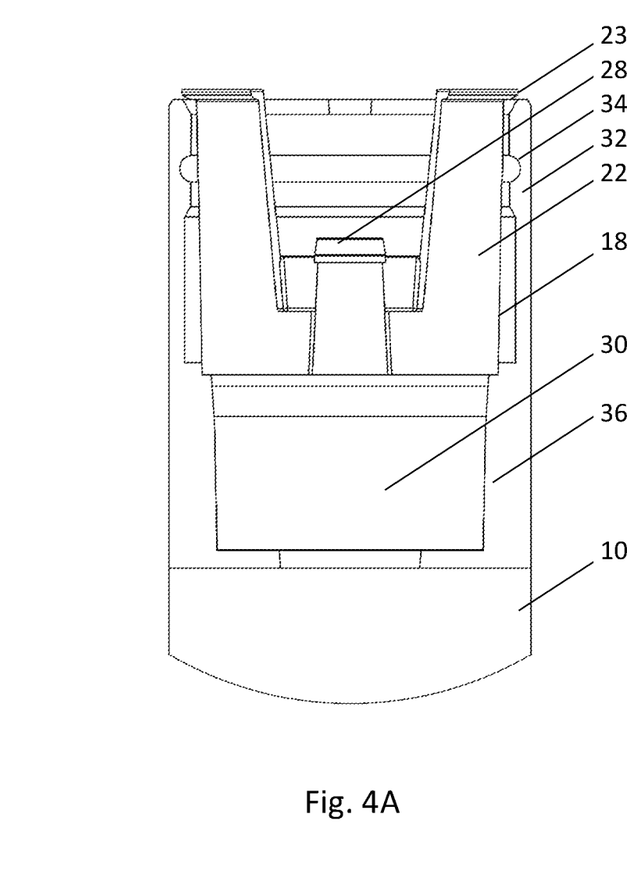
FIG. 4A is a cut-away front elevation of the nut and part of the dose selector housing in an initial configuration.

FIG. 4A shows the nut 18 when it is initially inserted into the opening of the cavity 30 in the distal end of the dose selector housing 10. The piston rod 16 (not shown) has previously been threaded through the nut. The nut 18 is oriented so that its axial channels 25 are aligned with the axial ribs 36 of the dose selector housing 10. The lip 23 of the nut 18 rests at the mouth of the cavity 30.

Figure 4B:
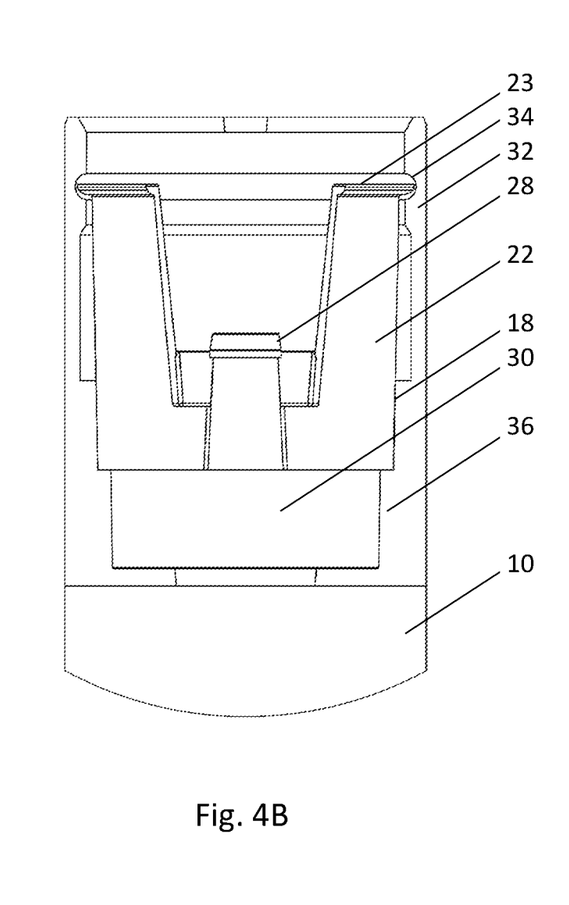
FIG. 4B is a cut-away front elevation of the nut and part of the dose selector housing in an intermediate configuration.

FIG. 4B shows the nut 18 after the initial assembly step, when it adopts an intermediate axial position in the dose selector housing 10. A jig (not shown) pushes the nut 18 to slide in the proximal direction from the initial position of FIG. 4A, the movement being guided by the axial channels 25 of the nut 18 following the axial ribs 36 of the dose selector housing 10. The nut alignment arms 22 flex inwards to allow the lip 23 to pass through the constricted neck 32 of the cavity 30. When the lip 23 reaches the annular indent 34 in the neck 32, the resilient alignment arms 22 spring back outwards so that the lip 23 lodges in the indent 34. When the jig is withdrawn, the nut 18 is releasably retained in the dose selector housing 10 to form a sub-assembly that is robust enough to be transported to another location for final assembly, while maintaining the relative positions of the various components. (Note that the sub-assembly preferably also includes the dose selector mechanism 12 and the piston rod 16 not shown in FIG. 4B.)

Figure 4C:
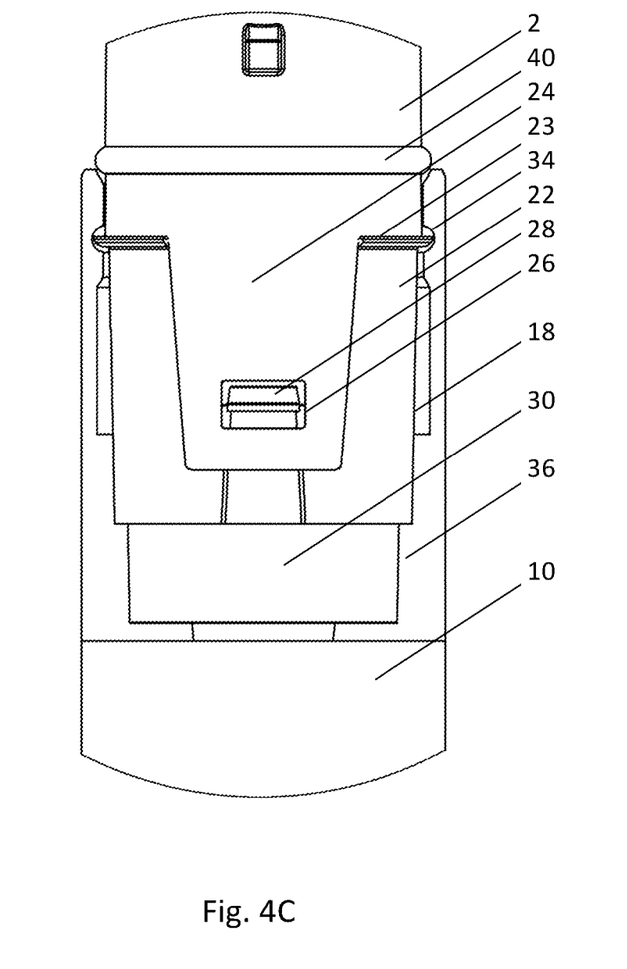
FIG. 4C is a cut-away front elevation of the nut, part of the dose selector housing and part of the cartridge housing in the intermediate configuration.
Figure 5A:
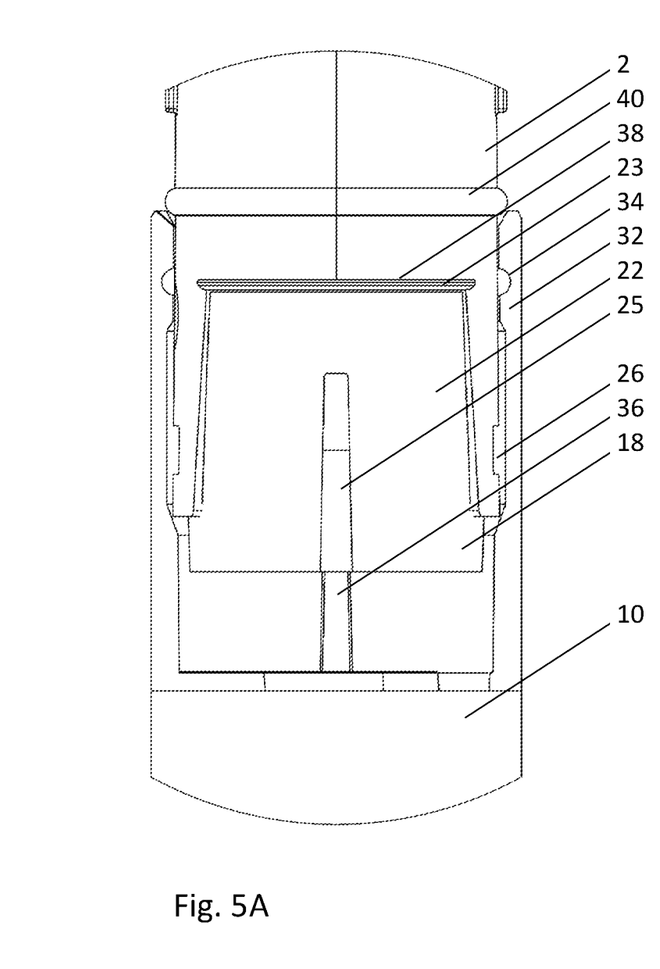
FIG. 5A is a cut-away side elevation of the intermediate configuration shown in FIG. 4C.

FIGS. 4C and 5A illustrate the first step in the final assembly of the injector pen, which involves fitting the drug cartridge 4 and cartridge housing 2 to the previously manufactured sub-assembly. The view in FIG. 4C corresponds to FIGS. 4A and 4B, while the view in FIG. 5A is rotated through 90°. The pre-filled drug cartridge 4 is first inserted into the cartridge housing 2 but for clarity it is not shown in these figures.

First the sub-assembly comprising the dose selector housing 10 and the nut 18 is firmly mounted then, using a second jig, the proximal end of the cartridge housing 2 is inserted into the cavity 30 in the distal end of the dose selector housing 10. The cartridge housing 2 is oriented such that the cartridge housing alignment arms 24 enter the gaps between the nut alignment arms 22 and interdigitate with them. Insertion of the cartridge housing 2 continues, being guided by the mutually engaging alignment arms 22,24 until an end surface 38 of the cartridge housing 2 abuts the ends of the nut alignment arms 22. In the illustrated embodiment, the interdigitating alignment arms 22,24 combine to form a substantially complete cylinder, which encloses the proximal end of the drug cartridge 4 and the distal end of the piston rod 16 (not shown). The clips 28 on the nut 18 snap into the recesses 26 of the cartridge housing 2 to engage the respective parts securely together. The nut 18 remains lodged in the intermediate axial position, with its lip 23 releasably retained by the annular indent 32. A protrusion, such as an annular bead 40, faces outwardly from an external surface of the cartridge housing and rests against the mouth of the cavity 30.

Figure 4D:
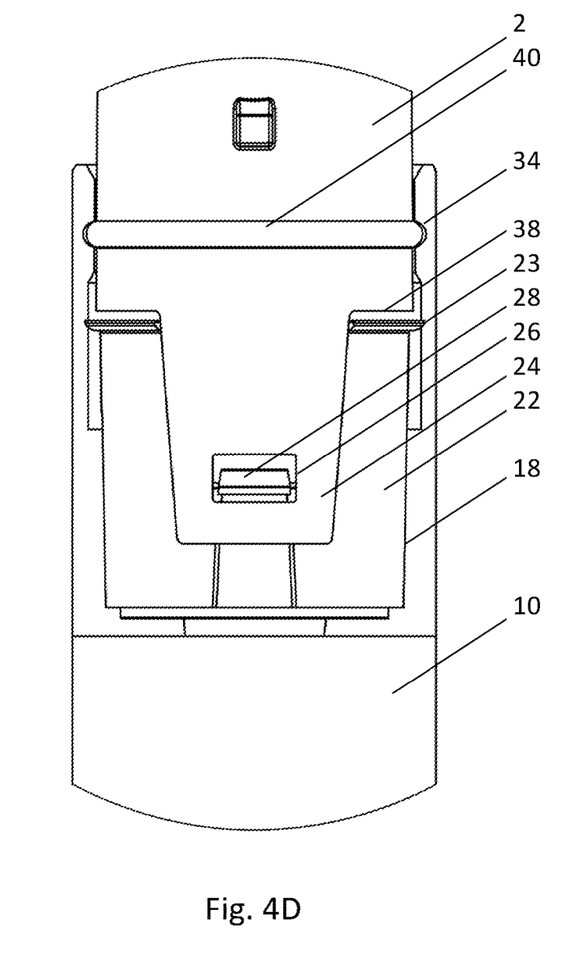
FIG. 4D is a cut-away front elevation of the nut, part of the dose selector housing and part of the cartridge housing in a final configuration.
Figure 5B:
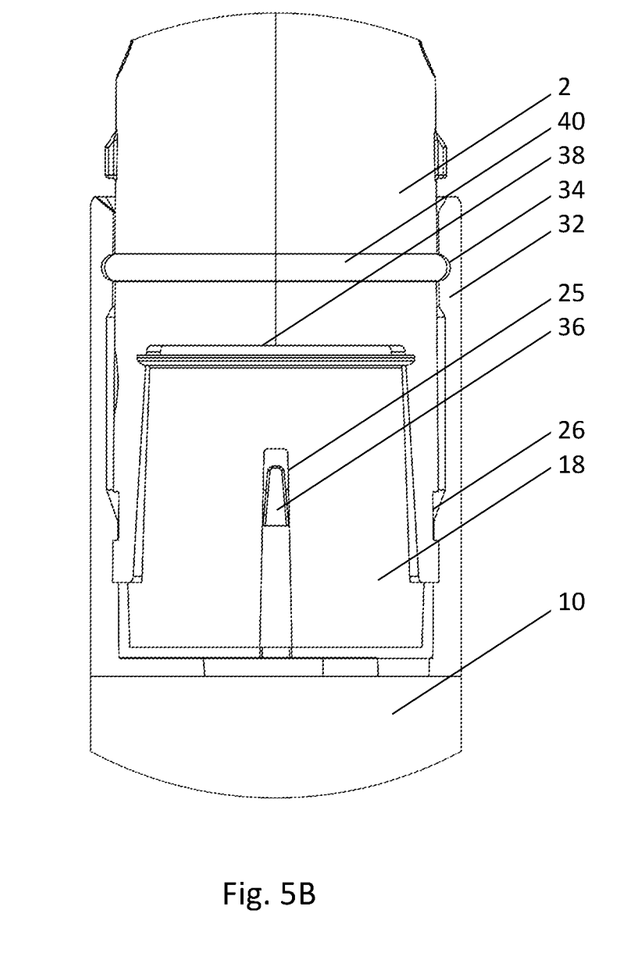
FIG. 5B is a cut-away side elevation of the final configuration shown in FIG. 4D.

FIGS. 4D and 5B illustrate the final step in the assembly of the injector pen. The views are the same as FIGS. 4C and 5A respectively.

The second jig (not shown) now pushes the cartridge housing 2 and the nut 18 in the proximal direction, further into the dose selector housing 10. The sliding movement is guided by the axial channels 25 of the nut 18 continuing to follow the axial ribs 36 of the dose selector housing 10. The jig is strong enough to force the lip 23 of the nut 18 out of the annular indent 34, even though the nut alignment arms 22 are no longer able to flex inwards. The jig is also strong enough to force the annular bead 40 of the cartridge housing 2 through the constricted neck 32 of the dose selector housing 10 until the bead reaches the annular indent 23. The cartridge housing 2 and nut 18 are now in their final axial position, as seen in FIGS. 4D and 5B, and the jig can be withdrawn. Engagement of the annular bead 40 in the annular indent 34 resists the cartridge housing 2 being pulled back out of the dose selector housing 10 during subsequent use of the pen. As previously noted, in the illustrated embodiment the piston rod 16 has a threaded engagement with the nut 18. When the pen has been primed for first use, the piston rod 16 thereafter exerts a pull on the nut 18 in the proximal direction, which in turn pulls the clips 28 tight within the recesses 26 of the cartridge housing 2.

It is preferred but not essential that the annular bead 40 should form a continuous ring about the external surface of the cartridge housing 2. Instead, it could comprise a number of outward protrusions forming a discontinuous ring. Similarly, it is preferred but not essential that the annular indent 34 in the dose selector housing 10 should form a continuous ring, provided that it can accommodate the lip 23 of the nut alignment arms 22 when the nut 18 is in the intermediate axial position, and the annular bead 40 (or alternative protrusions) of the cartridge housing 2 in the final axial position.

Although only one embodiment of the invention has been illustrated, variants of certain features have been described, which are considered to fall within the scope of the invention defined by the claims, and other practical variants will be apparent to the reader. Such variants may be used separately or in any combination to the fullest practical extent.

The invention claimed is:

1. A sub-assembly for an injector pen, comprising:
a dose selector housing, which comprises a distal end and a proximal end and which defines an axis from the distal end to the proximal end; and
a nut, of one-piece construction, comprising a first engagement means for engaging the dose selector housing, and a second engagement means for engaging a cartridge housing, the nut being configured to couple together the dose selector housing and the cartridge housing when the sub-assembly is assembled into an injector pen;
wherein:
the distal end of the dose selector housing defines an opening, through which the nut can be inserted to move along the axis through an intermediate axial position in the dose selector housing and reach a final axial position in the dose selector housing;
the first engagement means comprises a radially outwardly extending lip;
the dose selector housing comprises an inner surface, and a radially outwardly extending groove-shaped indent formed in the inner surface; and
when the nut is in the intermediate axial position, the radially outwardly extending lip of the first engagement means is releasably located in the radially outwardly extending groove-shaped indent formed in the inner surface of the dose selector housing.

2. The sub-assembly according to claim 1, wherein the nut comprises a set of at least two axially extending channels and the dose selector housing comprises a corresponding set of at least two axially extending ribs for engaging the channels to guide the axial movement of the nut into the dose selector housing.

3. The sub-assembly according to claim 1, further comprising a piston rod disposed along the axis, the nut being in threaded engagement with the piston rod.

4. The sub-assembly according to claim 1, wherein the nut comprises at least two arms that extend in the distal direction when the nut is in the intermediate axial position, the arms being capable of resilient, radially inward deformation, and the end of each arm carrying part of the radially outwardly extending lip.

5. An injector pen comprising the sub-assembly according to claim 4, and a cartridge housing, wherein the cartridge housing comprises a set of arms that extend in the proximal direction, the arms of the cartridge housing being equal in number to the arms of the nut and configured to interdigitate between them.

6. The injector pen according to claim 5, wherein the arms of the cartridge housing are provided with recesses, and wherein the engagement means of the nut comprise clips for engaging the recesses to secure the cartridge housing to the nut.

7. The injector pen according to claim 5, wherein the cartridge housing further comprises an outwardly facing protrusion that is configured to engage with the radially outwardly extending groove-shaped indent of the dose selector housing.

8. The sub-assembly for an injector pen, of claim 1, further comprising a cartridge housing, wherein the cartridge housing comprises cartridge housing engagement means configured to couple with the second engagement means.

9. The sub-assembly for an injector pen, of claim 8, wherein the cartridge housing is engaged with the second engagement means.

10. The sub-assembly for an injector pen, of claim 8, wherein the dose selector housing and the cartridge housing are coupled together with the nut.

11. A method of forming a sub-assembly for an injector pen, the sub-assembly comprising a dose selector housing and a nut for securing the sub-assembly to a cartridge housing, wherein
the nut is of a one-piece construction, comprises a first engagement means for engaging the dose selector housing, comprises a second engagement means for engaging the cartridge housing, and is configured to couple together the dose selector housing and the cartridge housing, and
the method comprises the steps of:
(a) inserting the nut into an opening in a distal end of the dose selector housing;
(b) moving the nut along an axis of the dose selector housing to an intermediate axial position in the dose selector housing; and
(c) engaging the nut with the dose selector housing by locating a radially outwardly extending lip of the first engagement means in a radially outwardly extending groove-shaped indent formed in an inner surface of the dose selector housing to releasably retain the nut at the intermediate axial position.

12. The method of claim 11, wherein the forming a sub-assembly occurs in a first location and the method further comprises transporting the sub-assembly from the first location to a second location, and securing a cartridge housing to the sub-assembly in the second location, wherein the securing a cartridge housing to the sub-assembly in the second location comprises:
(d) taking the sub-assembly, while the nut is releasably retained at the intermediate axial position, by the radially outwardly extending lip of the nut;
(e) inserting a cartridge housing into the opening in the distal end of the dose selector housing;
(f) using the cartridge housing to displace the nut from the intermediate axial position to a final axial position in the dose selector housing; and
(g) before, during, or after step (f), securely engaging the nut with the cartridge housing.

13. A method of assembling an injector pen comprising the steps of:
(d) providing a sub-assembly that comprises a dose selector housing and a nut, the nut being of one-piece construction, comprising a first engagement means for engaging the dose selector housing, comprising a second engagement means for engaging a cartridge housing, being configured to couple together the dose selector housing and the cartridge housing, and being releasably retained at an intermediate axial position in the dose selector housing by the first engagement means of the nut being located in a radially outwardly extending groove-shaped indent formed in an inner surface of the dose selector housing;
(e) inserting a cartridge housing into an opening in a distal end of the dose selector housing;
(f) using the cartridge housing to displace the nut from the intermediate axial position to a final axial position in the dose selector housing; and
(g) before, during, or after step (f), securely engaging the nut with the cartridge housing.

* * * * *